(12) United States Patent
Iwasaka et al.

(10) Patent No.: US 10,149,603 B2
(45) Date of Patent: Dec. 11, 2018

(54) ENDOSCOPE

(71) Applicant: FUJIFILM Corporation, Tokyo (JP)

(72) Inventors: Masayuki Iwasaka, Kanagawa (JP); Teruyuki Emura, Kanagawa (JP); Sunao Hachisuka, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 15/073,662

(22) Filed: Mar. 18, 2016

(65) Prior Publication Data

US 2016/0270636 A1   Sep. 22, 2016

(30) Foreign Application Priority Data

Mar. 20, 2015 (JP) ................... 2015-058350

(51) Int. Cl.
*A61B 1/00* (2006.01)
(52) U.S. Cl.
CPC ...... *A61B 1/00098* (2013.01); *A61B 1/00137* (2013.01); *A61B 1/0011* (2013.01)
(58) Field of Classification Search
CPC .................... A61B 1/00098; A61B 1/00101
USPC ................... 600/106, 107, 127, 133
See application file for complete search history.

(56) References Cited

U.S. PATENT DOCUMENTS

| | | | | | |
|---|---|---|---|---|---|
| 5,569,157 A | * | 10/1996 | Nakazawa | .......... | A61B 1/0008 600/104 |
| 5,730,701 A | * | 3/1998 | Furukawa | ........... | A61B 1/0008 600/121 |
| 2003/0073955 A1 | * | 4/2003 | Otawara | ............ | A61B 1/00098 604/164.01 |
| 2007/0270638 A1 | * | 11/2007 | Kitano | ............... | A61B 1/00098 600/104 |

FOREIGN PATENT DOCUMENTS

| | | | | |
|---|---|---|---|---|
| JP | 06-315458 | | 11/1994 | |
| JP | H08243076 | | 9/1996 | |
| JP | 2005348896 A | * | 12/2005 | ......... A61B 1/00098 |

OTHER PUBLICATIONS

"Office Action of Japan Counterpart Application," with machine English translation thereof, dated Oct. 5, 2018, p. 1-p. 6.

* cited by examiner

*Primary Examiner* — Alexandra L Newton
*Assistant Examiner* — Rynae Boler
(74) *Attorney, Agent, or Firm* — JCIPRNET

(57) ABSTRACT

Since a lower-surface side opening of an elevator housing slit is closed by a partition wall portion of a cap in normal operation, and a rotating shaft receiving portion of an elevator has a rotating shaft housing groove opened on the side opposite to the lower surface when the elevator is attached to a distal end portion body, the elevator is not removed structurally at an angle of the elevator when the treatment tool is operated to be stood, and a rotating shaft and the rotating shaft receiving portion do not have to be attached excessively tightly. Therefore, a work load in disassembling and assembling of a distal end portion can be set appropriately, and workability in disassembling and assembling is improved. Moreover, as a result, the distal end portion can be cleaned rapidly and easily.

6 Claims, 10 Drawing Sheets

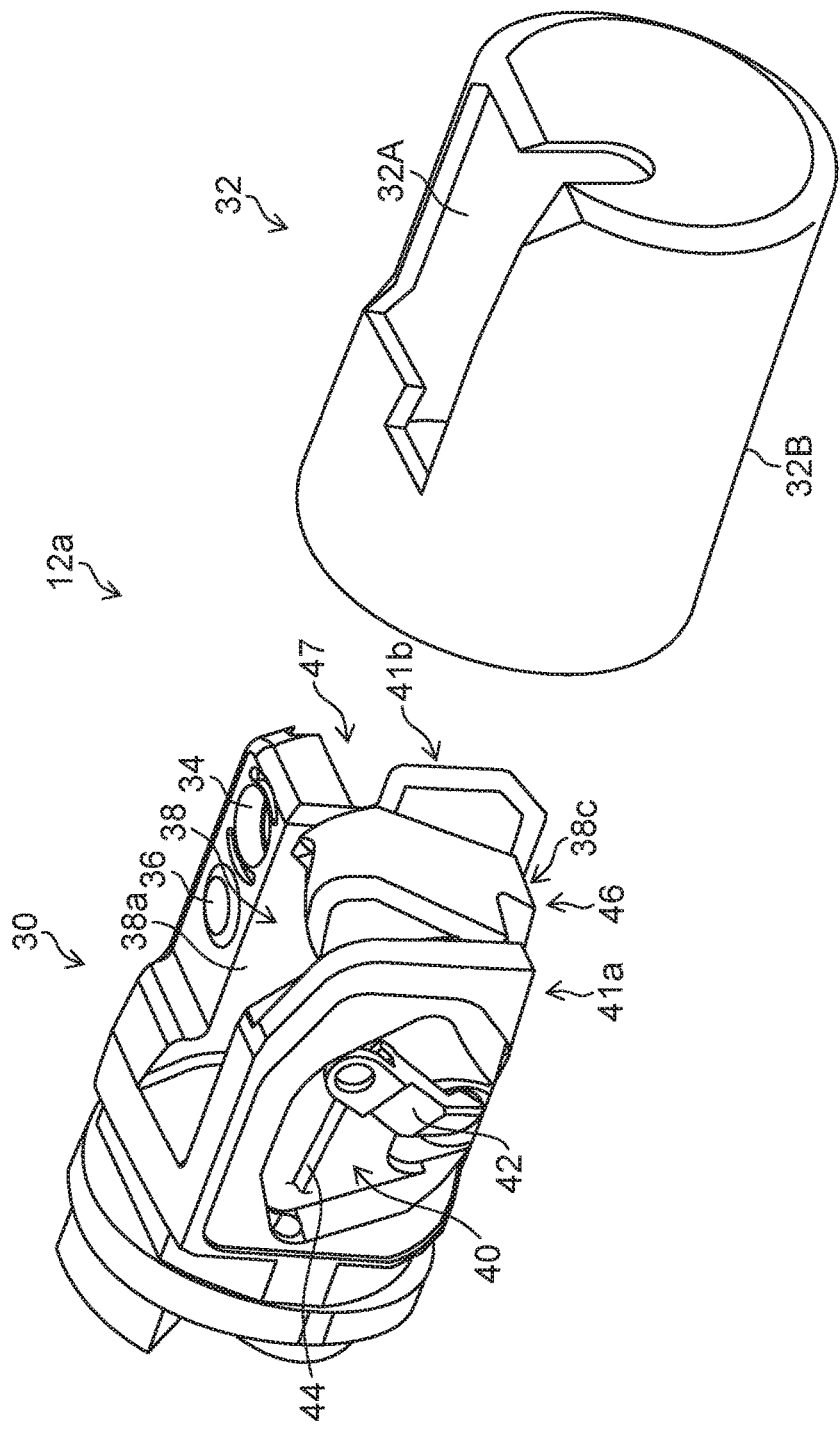

ENDOSCOPE

CROSS-REFERENCE TO RELATED APPLICATIONS

The present application claims priority under 35 U.S.C. § 119 to Japanese Patent Application No. 2015-058350, filed on Mar. 20, 2015. Each of the above application(s) is hereby expressly incorporated by reference, in their entirety, into the present application.

BACKGROUND OF THE INVENTION

Field of the Invention

The present invention relates to an endoscope and particularly to a structure of a distal end portion of an endoscope provided with an elevator (forceps elevator) for a treatment tool and an elevating mechanism (elevator erecting mechanism) for the elevator.

Description of the Related Art

Regarding the endoscope, various treatment tools are inserted into a treatment-tool entry port provided on an operation portion and they are led out of the treatment-tool exit port opened in the distal end portion and used for treatment. The treatment tools such as a guide wire, a contrast medium tube and the like are used for a duodenoscopy, puncture needles for an ultrasonic endoscope, and forceps, snares and the like for a direct-viewing endoscope or a side-viewing endoscope, for example. These treatment tools need to change a derivation direction at the distal end portion in order to treat a desired position in a subject, and thus, a treatment-tool elevating mechanism (forceps elevator, hereinafter referred to as an "elevator") is provided on the distal end portion.

As such the treatment-tool elevating mechanisms, a mechanism in which a wire is attached to the elevator and extended to a proximal end side of the endoscope, is known. In the mechanism, the elevator is rotated around a rotating shaft by pushing and pulling operation of the wire with an operation lever provided on the operation portion so as to change a position of the elevator between an erecting position and a reclining position. Moreover, a mechanism (lever type) in which the rotating shaft of the elevator is coupled with a housed lever through a partition wall, and the wire is attached to the lever is also known. In the mechanism, the elevator is rotated around the rotating shaft by means of the pushing and pulling operation of the wire with the operation lever provided on the operation portion so as to change the position of the elevator between the erecting position and the reclining position.

The distal end portion provided with such a treatment-tool elevating mechanism has a complicated shape and structure and thus, improvement of washing performances such as wraparound of a disinfectant, insertion of a washing brush (reachability of a tip end of the brush) or drainage and ease of a washing work are in demand. Conventionally an endoscope having a cap on the distal end portion and a detachable elevator is known (see Japanese Patent Application Laid-Open No. 6-315458, for example). In this type of endoscope, the cap and the elevator are removed after treatment, and the distal end portion is cleaned.

SUMMARY OF THE INVENTION

However, in the conventional endoscope described in Japanese Patent Application Laid-Open No. 6-315458, an erecting pin and an erecting pin slot are opened on a proximal end side of the distal end portion and thus, there is a concern that the elevator comes off to a distal end side during an operation depending on a degree of slotting. In order to prevent it, the slotting of the erecting pin needs to be set tightly. However, since the elevator is so small that a large force cannot be applied easily when attaching and detaching the elevator, if slotting is made too tight, workability of dissembling and assembling of the distal end portion becomes poor.

The present invention was made in view of such circumstances and aims to provide an endoscope which has a favorable workability at the time of dissembling and assembling of the distal end portion.

In order to achieve the aforementioned object, an endoscope according to a first aspect of the present invention includes: an insertion portion which has a distal end and a proximal end; an operation portion which is provided on a proximal end side of the insertion portion and includes an operating member; a distal end portion body which is provided on a distal end side of the insertion portion, and has a front surface being a surface in a longitudinal direction of the insertion portion, an upper surface being a surface in a direction in which a treatment tool is led out with respect to the longitudinal direction, and a lower surface being a surface on a side opposite to the upper surface with respect to the longitudinal direction; an elevator which is rotatably provided on the distal end portion body; a rotating shaft provided with an axis and configured to rotate the elevator around the axis, wherein a cross section perpendicular to a direction of the axis has a non-circular shape; a rotating shaft receiving portion which is provided on the elevator and has a rotating shaft housing groove opened to a side opposite to the lower surface when the elevator is attached to the distal end portion body; an elevator erecting mechanism which rotates the rotating shaft; an operation wire which has a proximal-end-side coupling portion coupled to the operating member and a distal-end-side coupling portion coupled to the elevator erecting mechanism, the operation wire configured to rotate the rotating shaft to recline or erect the elevator by being pushed or pulled by an operation of the operating member; an elevator housing slit which is provided on the distal end portion body and forms a space portion housing the elevator, the elevator housing slit including an opening on a side of the upper surface, on a side of the lower surface and on a side of the front surface; and a cap detachably provided on the distal end portion body, the cap which includes an opening window which opens a part of the opening on the side of the upper surface and a partition wall portion which closes a part of the opening on the side of the lower surface in a state in which the cap is attached to the distal end portion body, wherein in a state in which the cap is attached to the distal end portion body, assuming a thickness between a first bottom surface of the rotating shaft housing groove in the rotating shaft receiving portion, the first bottom surface being a surface on a side of the upper surface and a second bottom surface faced with the lower surface of the distal end portion body is "a", a gap distance between the rotating shaft and the partition wall portion of the cap is "b", a depth of the rotating shaft housing groove in a direction connecting the upper surface and the lower surface is "c", and a proximal end side thickness of the rotating shaft receiving portion is "d", following conditional expressions (1) to (3) are satisfied:

$$a < b \quad (1)$$

$$a + c > b \quad (2)$$

$$b > d \quad (3).$$

The term "proximal end side thickness (thickness on the side of the proximal end)" for the rotating shaft receiving portion refers to a distance from a side wall surface on the proximal end side of the rotating shaft housing groove to the proximal end of the elevator.

According to the first aspect of the present invention, a part of the opening on a side of the lower surface is closed by the partition wall portion of the cap in normal use, and the rotating shaft receiving portion of the elevator has the rotating shaft housing groove opened on the side opposite to the lower surface when the elevator is attached to the distal end portion body. Therefore, the elevator is not removed (comes off) structurally at an angle of the elevator when the treatment tool is operated to erect, and the rotating shaft and the rotating shaft receiving portion do not have to be attached excessively tightly. Therefore, a work load in disassembling and assembling of the distal end portion can be set appropriately, and workability in disassembling and assembling is improved. Moreover, as a result, the distal end portion can be cleaned rapidly and easily.

An endoscope according to a second aspect is so constituted that, in the first aspect, the elevator erecting mechanism includes an elevator erecting lever coupled to the rotating shaft, the distal-end-side coupling portion of the operation wire is coupled to the elevator erecting lever, and the operation wire rotates the rotating shaft to recline or erect the elevator through the elevator erecting lever by being pushed or pulled by an operation of the operating member.

The second aspect shows one aspect of an elevator erecting mechanism.

As described above, according to the endoscope of the present invention, workability at the time of disassembling and assembling of the distal end portion is favorable.

BRIEF DESCRIPTION OF THE DRAWINGS

FIG. 2 is a perspective view illustrating a configuration of a distal end portion of the endoscope according to the embodiment of the present invention;

FIGS. 3A and 3B are views illustrating a distal end portion of the endoscope according to the embodiment of the present invention, in which FIG. 3A is a view illustrating a state when seen from a distal end direction, and FIG. 3B is a view illustrating a state when seen from above;

DETAILED DESCRIPTION OF THE EMBODIMENTS

Figure 1:
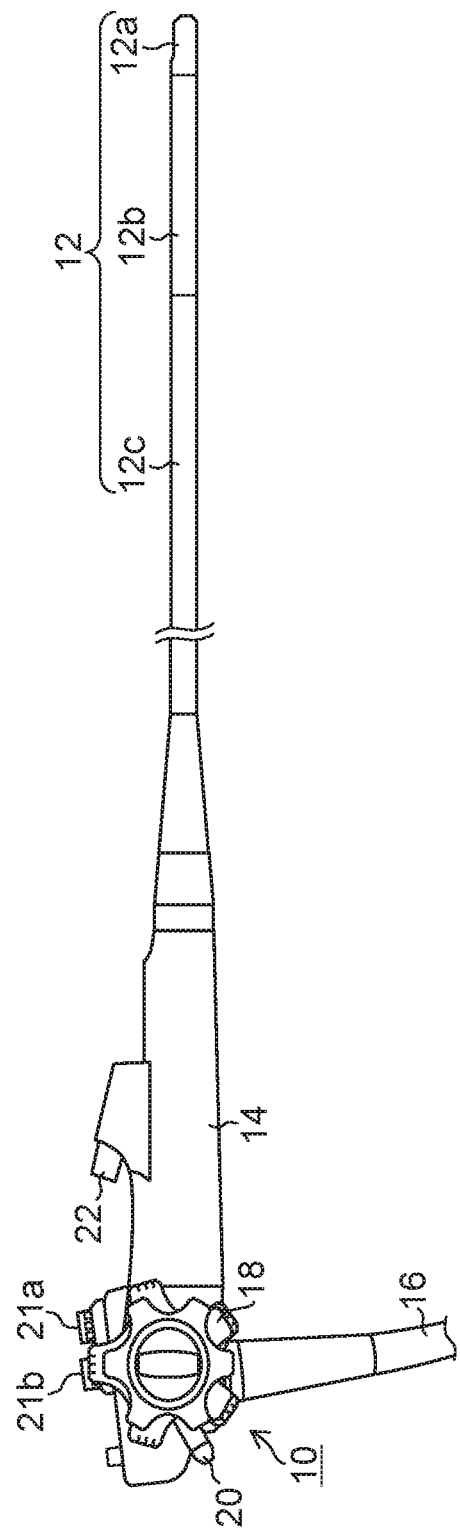
FIG. 1 is a view illustrating an entire configuration of an endoscope according to an embodiment of the present invention.

An endoscope according to the present invention will be described below by referring to the attached drawings. FIG. 1 is a view illustrating an entire configuration of the endoscope 10 according to the first embodiment.

<First Embodiment>
<Entire Configuration of Endoscope>

As illustrated in FIG. 1, the endoscope 10 includes an insertion portion 12 to be inserted into the body of a subject, and an operation portion 14 is coupled with a proximal end side of the insertion portion 12. To the operation portion 14, a universal cord 16 is connected, and the endoscope 10 is connected to a light source device, not shown, an image processing device (processor) and the like through this universal cord 16.

<Entire Configuration of Insertion Portion>

The insertion portion 12 is constituted by sequentially connecting a distal end portion 12a, a bending portion 12b, and a flexible portion 12c from the distal end side toward the proximal end side (operation portion 14 side). On a farthest proximal end side of the flexible portion 12c, a boot (boot member) for the insertion portion 12 is provided.

<Configuration of Operation Portion>

In the operation portion 14, an angle knob 18 which performs a bending operation of the bending portion 12b, an operation lever 20 which displaces (erects or reclines) the elevator 46 (see FIGS. 2, 4 and 6 to 11), an air/water supply button 21a which jets air, water and the like from an air/water supply nozzle provided on the distal end of the insertion portion 12, an suction button 21b and the like are provided. The operation lever 20 is an example of the operating member which operates the elevator. On the insertion portion 12 side of the operation portion 14, a treatment-tool entry port 22 into which various treatment tools such as forceps is inserted, is provided.

Figure 3A:
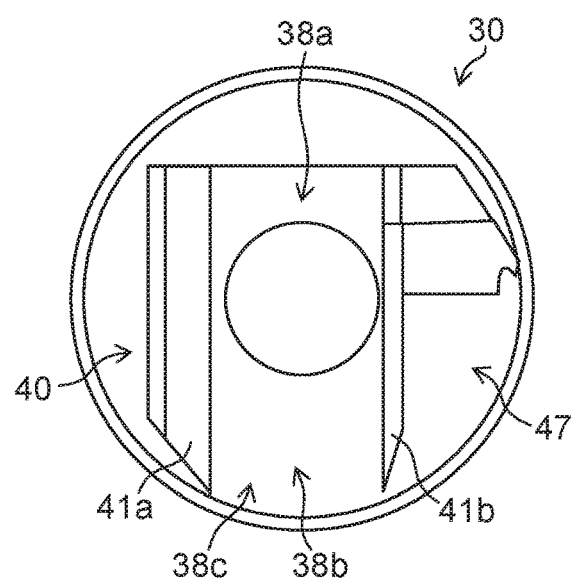
Figure 3B:
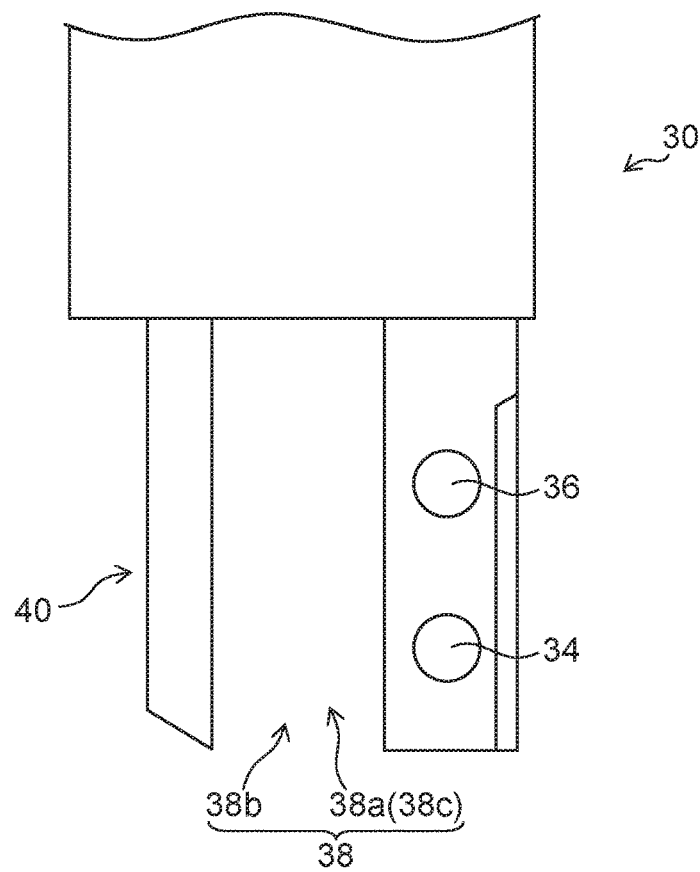

Moreover, in accordance with the operation of the air/water supply button 21a, air or water is supplied from an air/water supplying device built in the light source device, not shown, and is injected from the air/water supply nozzle toward an observation window 36 (see FIGS. 2 and 3). On the other hand, in accordance with the operation of the suction button 21b, suction is performed through an opening, not shown, provided on the distal end portion 12a. The distal end of the treatment tool inserted into the treatment-tool entry port 22 is led out from the opening of the distal end portion 12a through a forceps channel, not shown, communicating with the treatment-tool entry port 22, and a direction of the treatment tool can be changed by displacing (erecting or reclining) the elevator 46 by operating the operation lever 20.

<Configuration of Flexible Portion>

The flexible portion 12*c* has a configuration in which: the innermost side is a spiral tube formed by spirally braiding a thin band-shaped plate with elasticity on the innermost side, the spiral tube is then covered with a net-like body that is woven from a metal wire and fitted with a metal cap at both ends thereof to form a tubular body; the outer peripheral surface of the tubular body is laminated with an outer skin formed of resin.

<Configuration of Bending Portion>

The bending portion 12*b* has a configuration in which: a structural body is constituted by rotatably coupling angle rings, not shown, with each other; an outer periphery of this structural body is covered by a mesh body obtained by braiding a metal wire; and the mesh body is further covered by an outer skin made of rubber. Moreover, a plurality of wires, not shown, are extended from the angle knob 18 of the operation portion 14 to the bending portion 12*b*, and distal end portions of these wires are fixed to the distal end portions of the angle rings constituting the bending portion 12*b*. As a result, in accordance with the operation of the angle knob 18, the bending portion 12*b* is bent vertically and horizontally.

<Configuration of Distal End Portion>

FIG. 2 is an exploded perspective view illustrating a structure of the distal end portion 12*a* according to this embodiment. As illustrated in FIG. 2, the distal end portion 12*a* has a cap 32 covering a distal end portion body (body of the distal end portion) 30. In the cap 32, an opening window 32A which opens an opening portion (opening) 38*a* on the upper surface side of an elevator housing slit 38 (see FIGS. 2 to 4) and a partition wall portion 32B which closes an opening portion 38*c* on the lower surface side are formed, in a state where the cap 32 is attached to the distal end portion body 30. In the state where the cap 32 is attached, reclining of the elevator 46 is regulated by the partition wall portion 32B. Moreover, the cap 32 is made of a material with an elastic force or silicone rubber, for example, and by fitting a small diameter portion with a small inner diameter provided on a proximal end of the cap 32 into a groove formed in the distal end portion body 30, the cap 32 is detachably attached to the distal end portion body 30.

Figure 4:
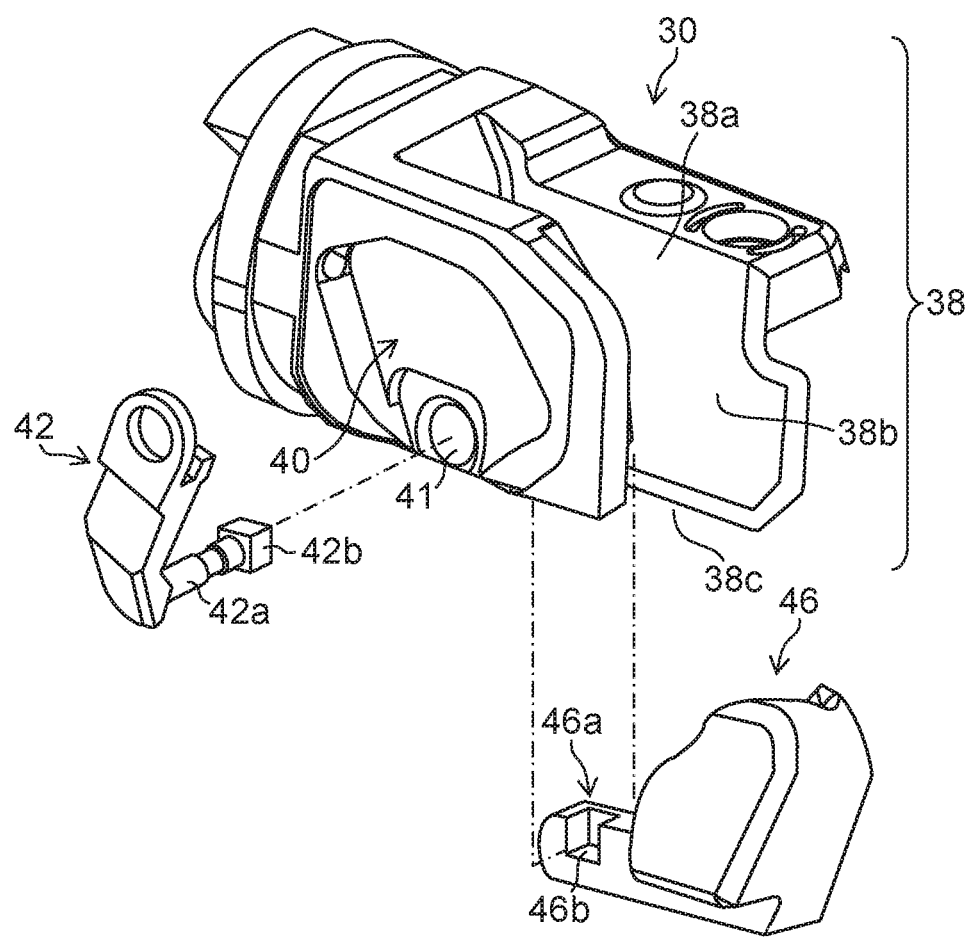
FIG. 4 is a view illustrating a state in which an elevator erecting lever and an elevator are connected in the endoscope according to the embodiment of the present invention.

The distal end portion body 30 is constituted by a metal with good erosion resistance such as stainless steel, and the elevator housing slit 38 (see FIGS. 2 to 4) is provided at a center position of the distal end portion body 30. This elevator housing slit 38 forms a space portion which houses the elevator 46. As illustrated in FIGS. 3 and 4, opening portions 38*a*, 38*b*, and 38*c* are opened and extends from the upper surface of the distal end portion body 30 (on the forceps (treatment tool) exit port side from the rotating shaft 42*a* of the elevator 46 as a starting point) to the lower surface (on a side opposite to the forceps (treatment tool) derivation direction from the rotating shaft 42*a* as the starting point) through the front surface (distal end side of the distal end portion body 30). Moreover, the distal end portion body 30 has a pair of side wall portions 41*a* and 41*b* faced with each other having the elevator housing slit 38 between them.

In FIGS. 2 to 4, in order to explicitly illustrate the opening portions 38*a*, 38*b*, and 38*c*, illustration of the cap 32, the elevator erecting lever 42, the elevator 46 and the like is omitted as appropriate.

As described above, in the endoscope 10 according to this embodiment, since the opening portions 38*a*, 38*b*, and 38*c* extending from the upper surface to the lower surface through the front surface are formed in the elevator housing slit 38, the exposed range of the elevator 46 is large, and the workability at the time of disassembling and assembling of the distal end portion is favorable. In addition, the distal end portion can be cleaned rapidly and easily.

Moreover, a treatment-tool insertion channel, not shown, communicates with the elevator housing slit 38. This treatment-tool insertion channel is inserted into the insertion portion 12 of the endoscope 10 and is connected to the treatment-tool entry port 22 of the operation portion 14. As a result, when the treatment tool is inserted into the treatment-tool insertion channel from the treatment-tool entry port 22, the treatment tool is guided to the elevator housing slit 38. The guided treatment tool is erected by the elevator 46 and is led out upward from the opening window 32A.

In one side wall portion 41*a* of the elevator housing slit 38, on a surface on a side opposite to the elevator 46, an erecting-lever housing chamber 40 is provided, and inside this erecting-lever housing chamber 40, an elevator erecting lever 42 which causes the elevator 46 to swing is housed. Moreover, on the side wall portion 41*b* on the side opposite to the erecting-lever housing chamber 40 having the elevator housing slit 38 between them, an optical-system housing chamber 47 is provided.

The optical-system housing chamber 47 is closed by attaching a protective cover, not shown, to the distal end portion body 30. A joint surface between the distal end portion body 30 and the protective cover is joined through a sealing agent, whereby a gap between the distal end portion body 30 and the protective cover is sealed, and airtightness of the optical-system housing chamber 47 is held.

On the upper part of the optical-system housing chamber 47, an illumination window 34 and the observation window 36 are disposed, and an air/water supply port, not shown, is provided toward the observation window 36. The air/water supply port is connected to an external device through an air/water supply tube (not shown) inserted into the insertion portion 12. Compressed air or water is injected from the air/water supply port toward the observation window 36 by operating the air/water supply button 21*a* of the operation portion 14, and the observation window 36 is cleaned. The illumination window 34, the observation window 36, and the air/water supply port are provided at a position facing the opening window 32A when the cap 32 is placed over the distal end portion body 30. Hereinafter, a surface on which the observation window 36 is disposed is referred to as an upper surface, and an observation direction observed from the observation window 36 is referred to as an upward.

Inside the optical-system housing chamber 47, an imaging optical system and an illumination optical system, not shown, are housed. The illumination optical system includes an illumination lens (not shown) which is installed on an inner side of the illumination window 34 and a light guide which is arranged so that a distal end the light guide faces this illumination lens. The light guide is inserted into the insertion portion 12 of the endoscope 10 and the proximal end portion thereof is connected to the light source device, not shown. As a result, an illumination light from the light source device is transmitted through the light guide and is projected upward from the illumination window 34.

The imaging optical system includes an objective lens disposed on an inner side of the observation window 36 and a CCD unit (Charge Coupled Device unit), not shown, disposed in the rear of this objective lens through a prism. The CCD unit is connected to an image processing device, not shown, through a cable. By means of this imaging optical system, a subject image taken in from the observation window 36 is converted to an electric signal and transmitted to the image processing device (processor) connected to the endoscope 10 and the subject image is displayed on a monitor through the image processing device.

On the other hand, the erecting-lever housing chamber 40 is closed by placing a protective plate, not shown, over the distal end portion body 30. The protective plate is screwed to the distal end portion body 30 at a plurality of spots (not shown), and a gap between the protective plate and the distal end portion body 30 is filled with a sealing agent. As a result, airtightness of the erecting-lever housing chamber 40 is maintained.

<Configuration of Elevator Erecting Lever and Elevator>

Inside the erecting lever housing chamber 40, the elevator erecting lever 42 is provided (see FIGS. 2 and 4). As illustrated in FIG. 4, the rotating shaft 42a provided on a lower end portion of the elevator erecting lever 42 is inserted into a circular hole 41, pivotally supported in a rotatable manner with respect to the distal end portion body 30, and constitutes the rotating shaft of the elevator 46.

Figure 5A:
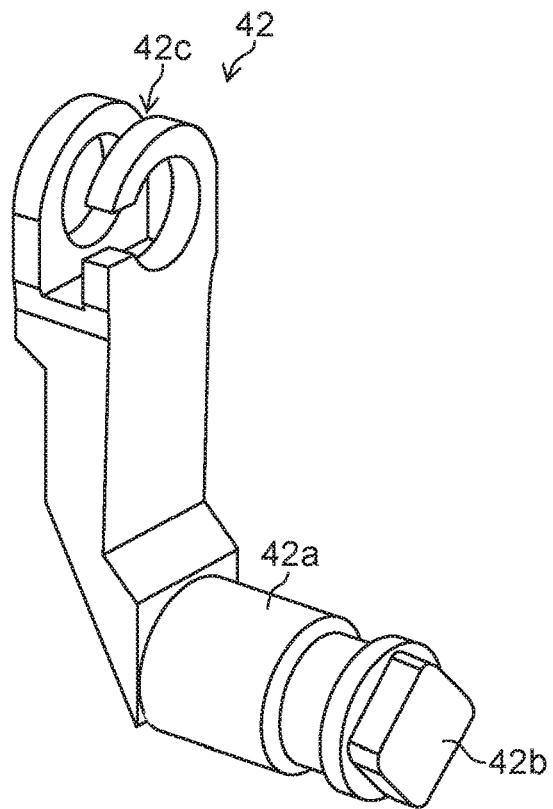
FIGS. 5A and 5B are views illustrating a shape of the elevator erecting lever in the endoscope according to the embodiment of the present invention.
Figure 5B:
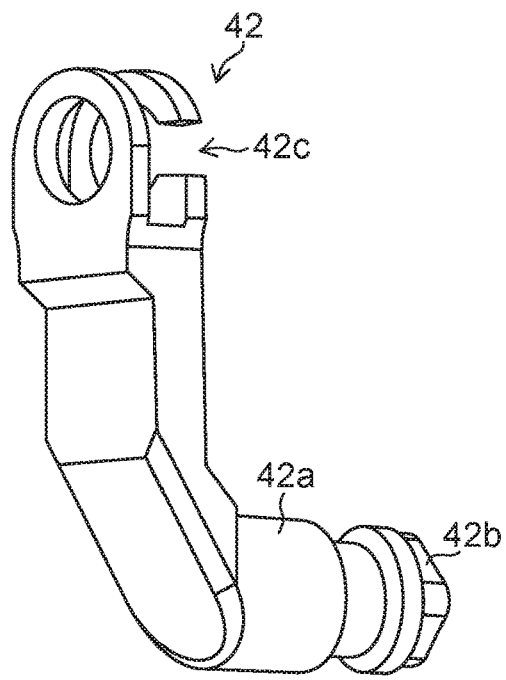

FIGS. 5A and 5B are views illustrating a shape of the elevator erecting lever 42. As illustrated in FIG. 5A and FIG. 5B, the elevator erecting lever 42 has the rotating shaft 42a having a circular section, and on a distal end of this rotating shaft 42a, a shaft distal end portion 42b having a rectangular section in a direction perpendicular to the rotating shaft 42a is formed.

Figure 6:
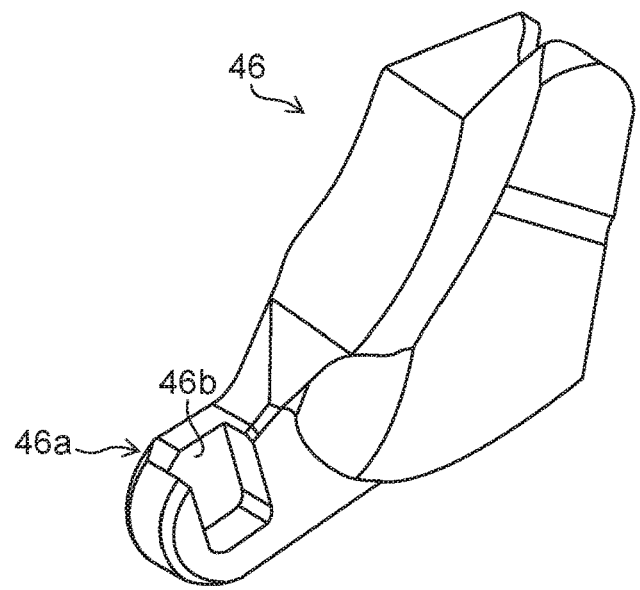
FIG. 6 is a view illustrating a shape of an elevator in the endoscope according to the embodiment of the present invention.

On the other hand, FIG. 6 is a view illustrating a shape of the elevator 46. As illustrated in FIGS. 4 and 6, the rotating shaft receiving portion 46a is provided on the elevator 46. The rotating shaft receiving portion 46a has a rotating shaft housing groove 46b opened on a side (upper surface side) opposite to the lower surface when the elevator 46 is mounted on the distal end portion body 30. This rotating shaft housing groove 46b is formed to have a rectangular shape with the size that can house a shaft distal end portion 42b of the elevator erecting lever 42. Therefore, when the shaft distal end portion 42b of the elevator erecting lever 42 is fitted in the rotating shaft receiving portion 46b of the elevator 46, the elevator erecting lever 42 is coupled to the elevator 46 and swings integrally with the elevator 46. That is, in this embodiment, the elevator erecting lever 42 constitutes an elevator erecting mechanism.

Moreover, as illustrated in FIG. 4, a distal-end-side coupling portion 44a of the operation wire 44 is coupled to an upper end portion 42c of the elevator erecting lever 42, and this operation wire 44 is inserted into the insertion portion 12, and the proximal-end-side coupling portion is coupled to the operation lever 20 of the operation portion 14. Therefore, by rotating/operating the operation lever 20, the operation wire 44 is push or pulled so as to rotate the elevator erecting lever 42, and as a result, the elevator 46 is displaced (erected or reclined).

<Connection State Between the Elevator Erecting Lever and Elevator>

Figure 7:
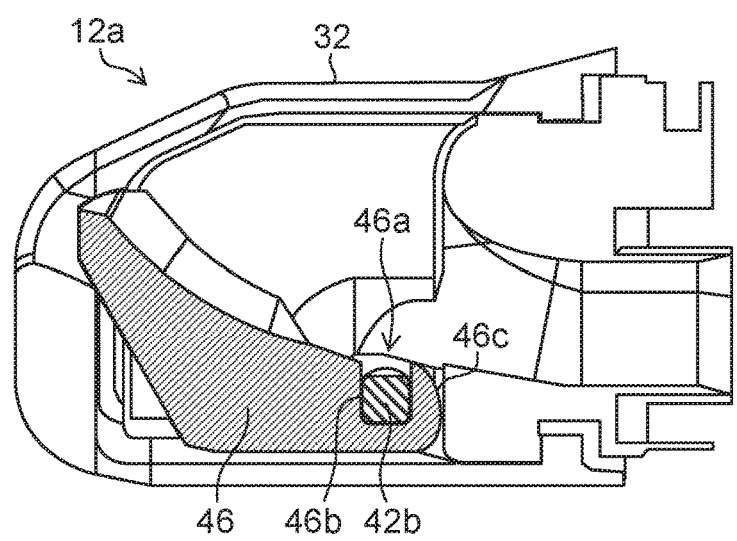
FIG. 7 is a sectional view illustrating a distal end portion in a state in which the elevator erecting lever and the elevator are connected in the endoscope according to the embodiment of the present invention.
Figure 8:
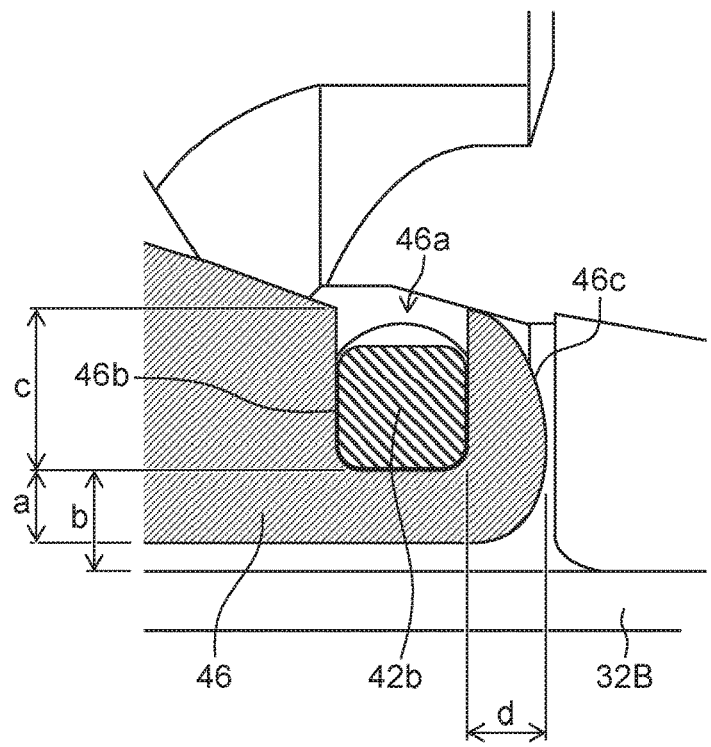
FIG. 8 is a partially enlarged view of the sectional view illustrated in FIG. 7.

FIG. 7 is a sectional view illustrating the distal end portion 12a in a state in which the elevator erecting lever 42 and the elevator 46 are coupled to each other, and the cap 32 is attached to the distal end portion body 30, and FIG. 8 is a partially enlarged view of the sectional view illustrated in FIG. 7.

As illustrated in FIGS. 7 and 8, in the endoscope 10 according to this embodiment, assuming that a thickness between a bottom surface of the rotating shaft housing groove 46b and a surface faced with the lower surface of the distal end portion body 30 is "a", a gap distance between the rotating shaft 42a and the partition wall portion 32B of the cap 32 is "b", a depth of the rotating shaft housing groove 46b is "c", and in a proximal end side thickness (a distance between the side wall surface on the proximal end side of the rotating shaft housing groove 46b and the proximal end of the elevator 46 in a direction (right-and-left direction in a state illustrated in FIGS. 7 and 8) connecting the distal end side and the proximal end side of the elevator 46) of the rotating shaft receiving portion 46a is "d", the following conditional expressions (1) to (3) are satisfied:

$$a < b \tag{1}$$

$$a + c > b \tag{2}$$

$$b > d \tag{3}$$

In this embodiment, since the thickness a of the rotating shaft housing groove 46b is smaller than the gap distance b between the rotating shaft 42a and the partition wall portion 32B of the cap 32 from the conditional expression (1), the elevator 46 can be housed in the cap 32, and since the sum of the thickness a and the depth c of the rotating shaft housing groove 46b is larger than the gap distance b from the conditional expression (2), removal of the elevator 46 to the direction of the lower surface is regulated. Therefore, at an angle (a range in which a reclining angle is smaller than a first reclining position which will be described later) of the elevator 46 when the erecting operation of the treatment tool is performed, the elevator 46 is not removed (comes off) structurally. Moreover, since the thicknesses a and d of the elevator are smaller than the gap distance b from the conditional expressions (1) and (3), the elevator 46 can be rotated in a state in which the cap 32 is attached to the distal end portion body 30. An end portion 46c of the elevator 46 is machined having a curved shape with a distance from the rotating shaft housing groove 46b not more than d so that the end portion 46c is not brought into contact with the partition wall portion 32B of the cap 32 when the elevator 46 is rotated.

<Attachment and Removal of Elevator>

At the angle of the elevator 46 when the erecting operation of the treatment tool is performed as described above, the elevator 46 is not removed structurally, and thus, removal of the elevator 46 from the distal end portion body 30 is performed by displacing the elevator 46 outside a reclining range (a first position or a second position which will be described later, see FIGS. 9 and 11) in the normal use. Moreover, attachment of the elevator 46 to the distal end portion body 30 is performed by housing the elevator 46 in the elevator housing slit 38 and fitting the shaft distal end portion 42b of the elevator erecting lever 42 with the rotating shaft receiving portion 46b of the elevator 46 (see FIG. 4). Such attachment of the elevator 46 can be also performed in a state corresponding to the first position or the second position.

<Reclining Position of Elevator>

Figure 9:
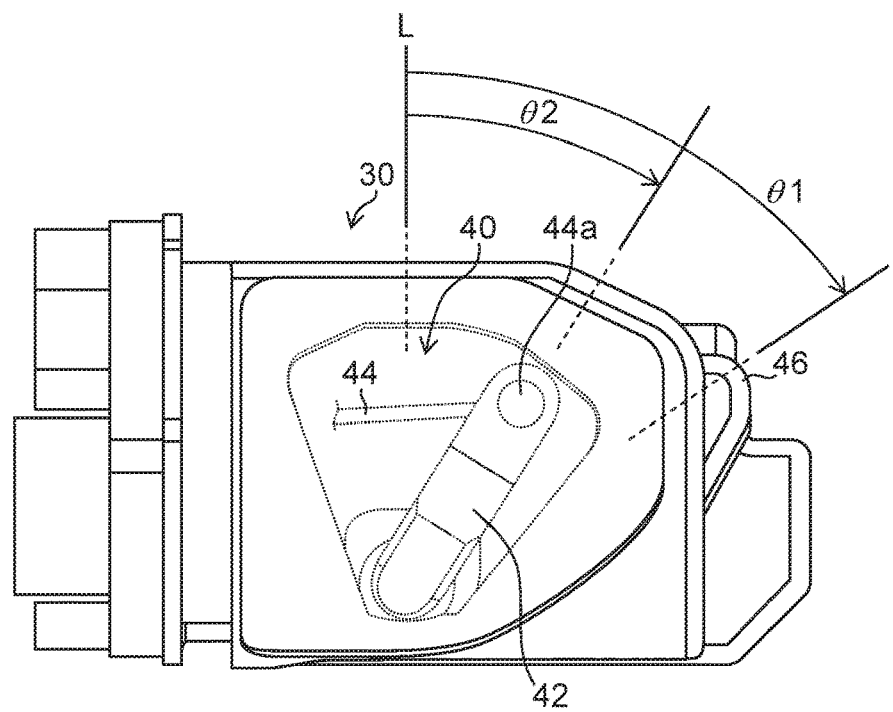
FIG. 9 is a view illustrating a state in which the distal end portion of the endoscope according to the embodiment of the present invention is seen from a side surface direction (elevator erecting lever side)

FIG. 9 is a view illustrating the distal end portion 12a in a state in which the elevator 46 is at the first reclining position (a position where the cap 32 is attached to the distal end portion body 30 and immediately before the elevator 46 is reclined toward the distal end side and is brought into contact with the partition wall portion 32B of the cap 32). The endoscope 10 is used in a state in which the erecting lever housing chamber 40 is covered by a protective plate as described above, but in FIG. 9, in order to explicitly illustrate the reclining state of the elevator erecting lever 42, the protective plate is not shown, and the erecting lever housing chamber 40 covered with the protective plate and the elevator erecting lever 42 and the like are indicated by dot lines (the same applies to FIGS. 10 and 11). In FIG. 9, the cap 32 is not shown, and in FIG. 10, the cap 32 is shown. As described above, the opening portions 38a, 38b, and 38c which extend from the upper surface to the lower surface through the front surface in the elevator housing slit 38 are formed. The reclining of the elevator 46 is restricted by the partition wall portion 32B in the normal use as described above. Moreover, since a stopper mechanism 60 (which will be described later) is provided on the operation portion 14, the elevator 46 is prevented from reclining toward the lower surface side larger than (over) the state illustrated in FIGS. 9 and 10.

Figure 10:
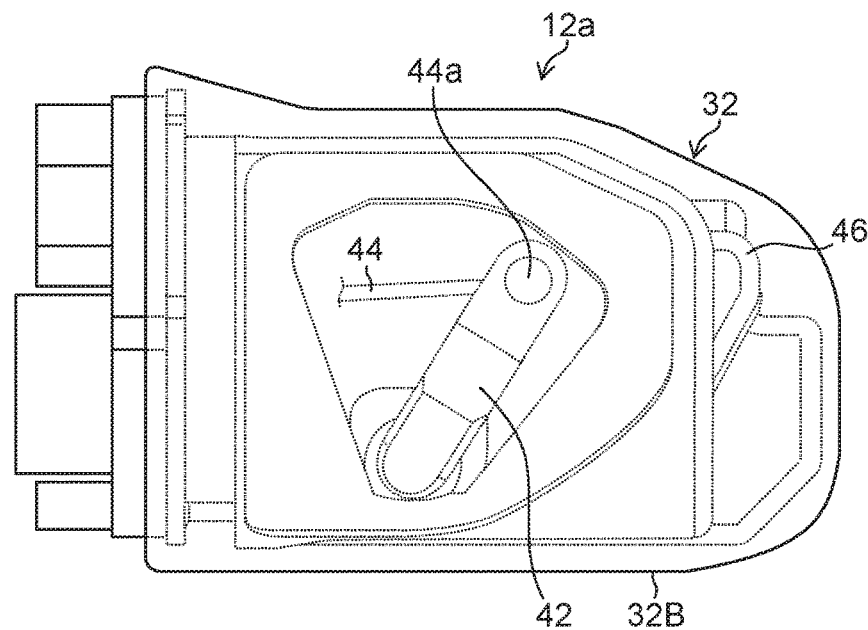
FIG. 10 is another view illustrating a state in which the distal end portion of the endoscope according to the embodiment of the present invention is seen from the side surface direction.
Figure 11:
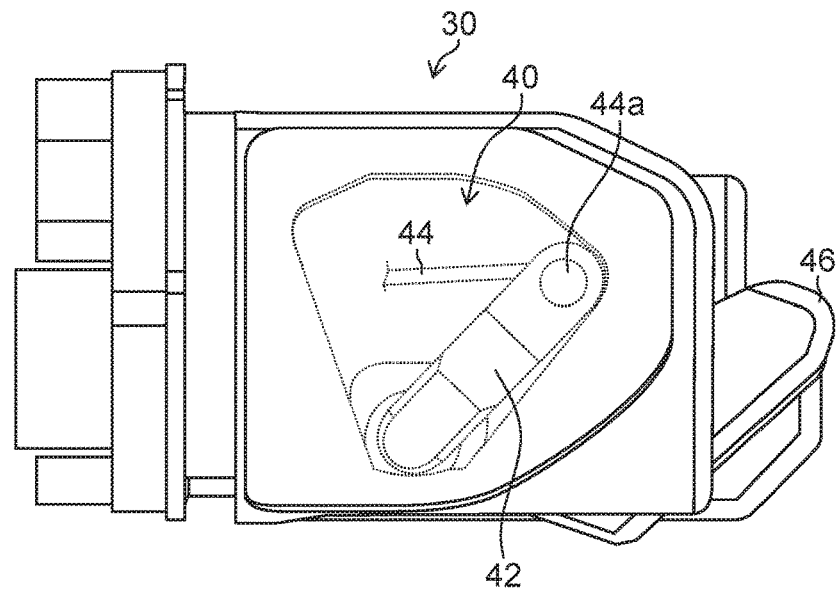
FIG. 11 is still another view illustrating a state in which the distal end portion of the endoscope according to the embodiment is seen from the side surface direction of the present invention.

On the other hand, FIG. 11 illustrates a state in which the cap 32 is removed, and moreover, the elevator 46 is displaced (further reclined toward the lower surface side) toward a side opposite to the erecting position larger than the state (first reclining position) in FIGS. 9 and 10 so as to be at the second reclining position by a second operation (which will be described later) of the operation lever 20. In the state in FIG. 11, exposure of the elevator 46 (exposure of the side surface portion) from the elevator housing slit 38 increases more than the state in FIGS. 9 and 10, and thus, a range that can be gripped by the hand of the operator or a jig increases, and attachment and removal of the elevator 46 to and from the distal end portion body 30 can be performed rapidly and easily.

<Elevator Erecting Lever and Reclining Angle of Elevator>

As illustrated in FIG. 9, in the endoscope 10 according to this embodiment, a reclining angle θ1 of the elevator 46 is larger than a reclining angle θ2 (an angle based on a direction L orthogonal to the axial direction of the endoscope 10) of the elevator erecting lever 42 (θ1>θ2). Assuming that the reclining angle θ1≤θ2, in order to largely recline the elevator 46 (to the second reclining position illustrated in FIG. 10, for example), the elevator erecting lever 42 also needs to be largely reclined. Therefore, the erecting-lever housing chamber 40 should be made large in order to ensure a rotation space of the elevator erecting lever 42. However, in the endoscope 10 according to this embodiment, by setting the reclining angles θ1 and θ2 in a relation as described above, the reclining angle θ1 of the elevator 46 can be made larger than the reclining angle θ2 of the elevator erecting lever 42, and the rotation space of the elevator erecting lever 42 is reduced, and the erecting lever housing chamber 40 and the distal end portion body 30 including it and the distal end portion 12a can be downsized.

<Stopper Mechanism>

Figure 12:
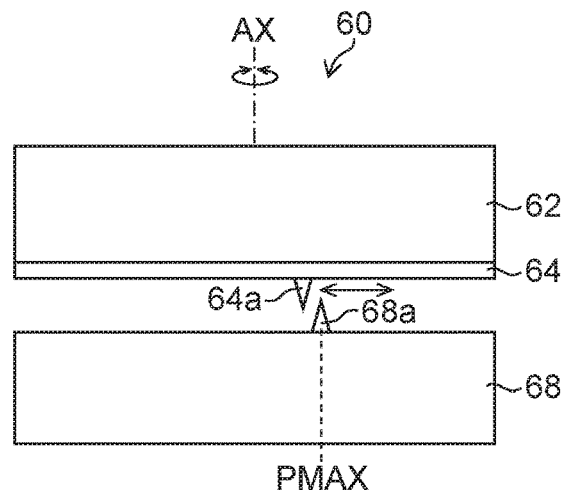
FIG. 12 is a conceptual diagram illustrating a stopper mechanism of the elevator provided on an operation portion of the endoscope according to the embodiment of the present invention.

Subsequently, a stopper mechanism (locking mechanism) of the elevator will be described. FIG. 12 is a conceptual diagram illustrating a structure of the stopper mechanism 60. As illustrated in FIG. 12, in the endoscope 10, a movable portion 62 which is rotatable around an axis AX in conjunction with (in interlock with) the rotating operation of the operation lever 20 is provided in the operation portion 14, and to a lower surface of this movable portion 62, a plate spring 64 including a projection 64a is attached. On the other hand, on a fixed portion 68 provided in a fixed manner on the body side of the operation portion 14, a stopper 68a is provided on a surface facing the movable portion 62.

The stopper 68a is provided at a position PMAX corresponding to the first reclining position of the elevator 46. Therefore, by rotating the operation lever 20 so as to allow the projection 64a to engage with the stopper 68a, one end of the rotation range of the elevator 46 is restricted (locked) to the first reclining position. Such operation of the operation lever 20 is referred to as the "first operation" hereinafter.

Therefore, in order to make the elevator 46 further recline over the first reclining position, an operation different from the rotating operation in the normal use of the operation lever 20 (an operation to intentionally apply a force larger than the normal use to further recline the elevator 46: hereinafter referred to as the "second operation") needs to be performed to the operation lever 20, and thus, the reclining from the first reclining position toward the second reclining position (position further displaced to a side opposite to the erecting position from the first reclining position; the state illustrated in FIG. 11) is restricted, and unintended reclining of the elevator 46 and resulting breakage of the cap 32 can be prevented. Moreover, by performing the second operation, the projection 64a rides over the stopper 68a, and engagement between the projection 64a and stopper 68a is unlocked, whereby the elevator 46 is reclined (larger than) over the first reclining position to reach the second reclining position. In this state, the exposure of the elevator 46 from the elevator housing slit 38 (exposure of the side surface portion) is larger than the states in FIGS. 9 and 10, and attachment and removal of the elevator 46 to and from the distal end portion body 30 can be performed rapidly and easily.

In the stopper mechanism 60, the number and size of the projection 64a or the stopper 68a may be determined in accordance with intensity of a required locking force.

Effects of this Embodiment

As described above, in the endoscope 10 according to this embodiment, attachment and removal of the elevator 46 to and from the distal end portion body 30 can be performed rapidly and easily, and workability of disassembling and assembling of the distal end portion 12a is favorable. Moreover, as a result, the distal end portion 12a can be cleaned rapidly and easily.

<Another Invention>

Figure 13:
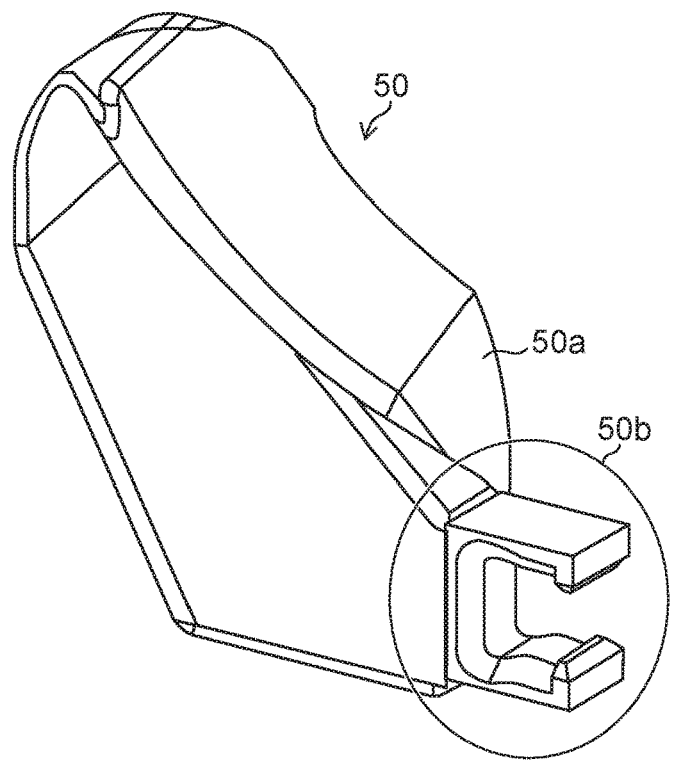
FIG. 13 is a view illustrating an example of the elevator according to another invention.
Figure 14:
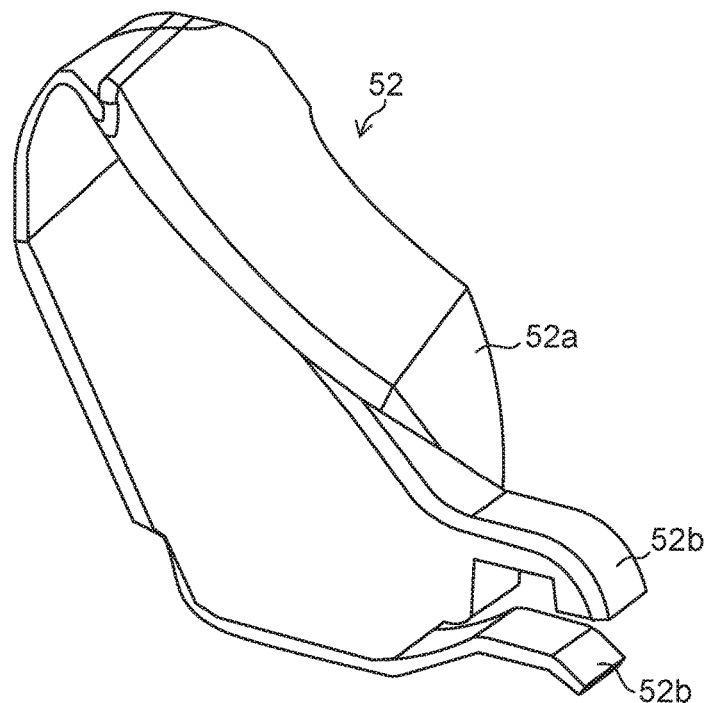
FIG. 14 is a view illustrating another example of the elevator according to another invention.
Figure 15:
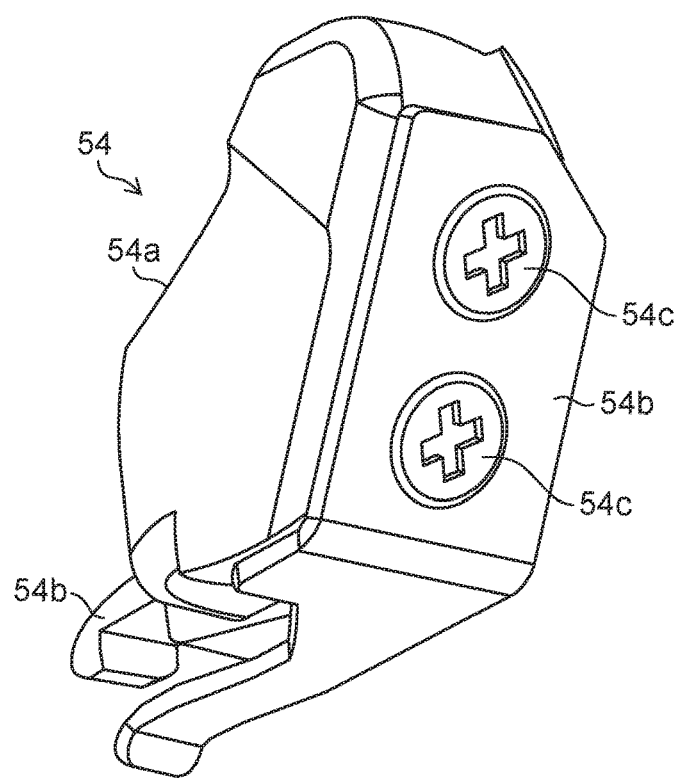
FIG. 15 is a view illustrating still another example of the elevator according to another invention.

Subsequently, an endoscope according to another invention other than the present invention will be described. In the embodiment of the present invention, the rotating shaft housing groove 46b of the elevator 46 and the rotating-shaft distal end portion 42b of the elevator erecting lever 42 are fitted together, but in the another invention, a mode of connection between the elevator 46 and the elevator erecting lever 42 is different from the present invention. An embodiment of a shape of the elevator in this another invention is illustrated in FIGS. 13 to 15. In the endoscope according to the another invention, since the configuration similar to the present invention can be employed for those other than the shape of the elevator, detailed explanation will be omitted.

FIG. 13 is a view illustrating an elevator 50 as an embodiment of the another invention. In the elevator 50, an elevator body 50a and a clip 50b (a circle mark portion in FIG. 13) are integrated by bonding or the like, and the elevator 50 is attached and fixed to the elevator erecting lever 42 by using elastic deformation and an urging force of the clip 50b to the rotating-shaft distal end portion 42b. Specifically, in the elevator 50, the clip 50b is fitted with the shaft distal end portion 42b and attached to the elevator erecting lever 42. At this time, since the clip 50b is elastically deformed by the rotating-shaft distal end portion 42b and presses the rotating-shaft distal end portion 42b by the urging force after the attachment from the upper surface side and lower surface side, the elevator 50 can be fixed to the elevator erecting lever 42. Moreover, by constituting such that the clip 50b is elastically deformable more largely than the rotating-shaft distal end portion 42b, the elevator 50 can be removed from the elevator erecting lever 42. A mode of such attachment and removal, and fixation is similar to elevators 52 and 54 illustrated in FIGS. 14 and 15.

FIG. 14 is a view illustrating the elevator 52 as another embodiment of another invention. In the elevator 52, a plate spring 52b is integrated with an elevator body 52a by welding, and the elevator 52 is attached and fixed to the elevator erecting lever 42 by using elastic deformation and an urging force of the plate spring 52b applied to the rotating-shaft distal end portion 42b.

FIG. 15 is a view illustrating the elevator 54 as still another embodiment of another invention. In the elevator 54, a plate spring 54b is integrated with the an elevator body 54a by screwing, and the elevator 54 is attached and fixed to the elevator erecting lever 42 by using elastic deformation and an urging force of the plate spring 54b applied to the rotating-shaft distal end portion 42b. The mode illustrated in FIG. 15 can further improve strength than the mode in FIG. 14.

In the elevators 50, 52, and 54 of the modes, the clip 50b, the plate springs 52b and 54b are elastically deformed by the rotating-shaft distal end portion 42b and thus, attachment and removal to and from the shaft distal end portion 42b is easy, workability of disassembling and assembling of the distal end portion 12a is favorable, and reliable fixation to the shaft distal end portion 42b can be realized by the urging forces of the clip 50b, the plate springs 52b and 54b. In each of the modes of another invention described above, intensities of the elastic deformation and the urging forces of the clip 50b, the plate springs 52b and 54b can be determined in accordance with a demand for easiness of attachment and removal, or strength of fixation of the elevators 50, 52, and 54 to the elevator erecting lever 42.

The present invention and another invention are not limited to the embodiments described above but are capable of various variations within a range not departing from the spirit of each invention.

What is claimed is:

1. An endoscope, comprising:
an insertion portion which has a distal end and a proximal end;
an operation portion which is provided on a proximal end side of the insertion portion and includes an operating member;
a distal end portion body which is provided on a distal end side of the insertion portion, and has a front surface being a surface in a longitudinal direction of the insertion portion, an upper surface being a surface in a direction in which a treatment tool is led out with respect to the longitudinal direction, and a lower surface being a surface on a side opposite to the upper surface with respect to the longitudinal direction;
an elevator which is rotatably provided on the distal end portion body;
a rotating shaft provided with an axis and configured to rotate the elevator around the axis, wherein a tip end of the rotating shaft having a cross section perpendicular to a direction of the axis has a non-circular shape;
a rotating shaft receiving portion which is provided on the elevator and has a rotating shaft housing groove having an upper fitting opening opened to a side opposite to the lower surface when the elevator is attached to the distal end portion body, wherein the rotating shaft housing groove has a wall blocking the rotating shaft from penetrating through the elevator in the direction of the axis of the rotating shaft, wherein the rotating shaft housing groove has a shape and a size to engage with the tip end of the rotating shaft so that the rotating shaft is coupled to the elevator and rotate together with the elevator, wherein a width of the upper fitting opening is equal to a width of the tip end of the rotating shaft;
an elevator erecting mechanism which rotates the rotating shaft; an operation wire which has a proximal-end-side coupling portion coupled to the operating member and a distal-end-side coupling portion coupled to the elevator erecting mechanism, the operation configured to rotate the rotating shaft to recline or erect the elevator by being pushed or pulled by an operation of the operating member;
an elevator housing slit which is provided on the distal end portion body and forms a space portion housing the elevator, the elevator housing slit including an upper opening on a side of the upper surface, a lower opening on a side of the lower surface and a front opening on a side of the front surface; and
a cap detachably provided on the distal end portion body, the cap which includes an opening window which opens a part of the opening on the side of the upper surface and a partition wall portion which closes a part of the opening on the side of the lower surface in a state in which the cap is attached to the distal end portion body, wherein
in a state in which the cap is attached to the distal end portion body, assuming a thickness between a first bottom surface of the rotating shaft housing groove in the rotating shaft receiving portion, the first bottom surface being a surface on a side of the upper surface and a second bottom surface faced with the lower surface of the distal end portion body is "a", a gap distance between the rotating shaft and the partition wall portion of the cap is "b", a depth of the rotating shaft housing groove in a direction connecting the upper surface and the lower surface is "c", and a proximal end side thickness of the rotating shaft receiving portion is "d", following conditional expressions (1) to (3) are satisfied:

$$a<b \qquad (1)$$

$$a+c>b \qquad (2)$$

$$b>d \qquad (3).$$

2. The endoscope according to claim 1, wherein:
the elevator erecting mechanism includes an elevator erecting lever coupled to the rotating shaft;
the distal-end-side coupling portion of the operation wire is coupled to the elevator erecting lever; and
the operation wire rotates the rotating shaft to recline or erect the elevator through the elevator erecting lever by being pushed or pulled by an operation of the operating member.

3. The endoscope according to claim 1, wherein the elevator erecting mechanism has an elevator erecting lever coupled with the elevator, and a reclining angle of the elevator when reclined by the elevator erecting lever and coupled to the rotating shaft is larger than a reclining angle of the elevator erecting lever.

4. The endoscope according to claim 1, wherein when a position where the elevator abuts on the partition wall portion of the cap is assumed to be a first reclining position in a state in which the cap is attached to the distal end portion body, and a position where the elevator is displaced from the first reclining position toward a side opposite to the erecting position is assumed to be a second reclining position in a state in which the cap is removed from the distal end portion body, the operating member displaces the elevator to the first reclining position when a first operation is performed and displaces the elevator to the second reclining position when a second operation is performed, and wherein the operation portion has a locking portion provided on the operating member and a stopper which is configured to restrict one end of a rotation range of the elevator to the first reclining position by engaging with the locking portion when the first operation is performed, and when the second operation is performed, the locking portion rides over the stopper and the engagement between the locking portion and the stopper is unlocked so as to allow movement of the elevator toward the second reclining position, wherein the locking portion and the stopper are protrusions protruding in opposite directions.

5. The endoscope according to claim 3, wherein:

the elevator erecting mechanism includes the elevator erecting lever coupled to the rotating shaft;

the distal-end-side coupling portion of the operation wire is coupled to the elevator erecting lever; and the operation wire rotates the rotating shaft to recline or erect the elevator through the elevator erecting lever by being pushed or pulled by an operation of the operating member.

6. The endoscope according to claim 4, wherein:

the elevator erecting mechanism includes the elevator erecting lever coupled to the rotating shaft;

the distal-end-side coupling portion of the operation wire is coupled to the elevator erecting lever; and the operation wire rotates the rotating shaft to recline or erect the elevator through the elevator erecting lever by being pushed or pulled by an operation of the operating member.

* * * * *